United States Patent [19]

Okamoto et al.

[11] Patent Number: 4,642,393
[45] Date of Patent: Feb. 10, 1987

[54] PROCESS FOR PREPARING 1,4-DIHYDROXY, 5,8-DIHYDRONAPHTHALENE AND RELATED COMPOUNDS

[75] Inventors: Yoshiyuki Okamoto, Fort Lee, N.J.; Richard Vicari, Astoria, N.Y.

[73] Assignee: Koppers Company, Inc., Pittsburgh, Pa.

[21] Appl. No.: 708,655

[22] Filed: Mar. 6, 1985

[51] Int. Cl.$^4$ .............................................. C07C 39/14
[52] U.S. Cl. ..................................... 568/734; 568/732
[58] Field of Search ................ 568/727, 734, 736, 732

[56] References Cited

U.S. PATENT DOCUMENTS 3,860,612  1/1975  Heiba et al. .......................... 568/736
4,510,337  4/1985  Cobbs et al. ......................... 568/734

OTHER PUBLICATIONS

Noller, "Chemistry of Organic Compounds", pp. 884, 927 and 943, 3rd Ed., Saunders Co., Phila. (1965).

Primary Examiner—Werren B. Lone
Attorney, Agent, or Firm—Herbert J. Zeh, Jr.

[57] ABSTRACT

1,4-dihydroxy, 5,8-dihydronaphthalene and related compounds are provided from benzoquinone, and 1,3-butadiene which may be substituted with halogen, acyl, and alkyl, in a one step reaction in the presence of a ferric salt catalyst.

7 Claims, No Drawings

PROCESS FOR PREPARING 1,4-DIHYDROXY, 5,8-DIHYDRONAPHTHALENE AND RELATED COMPOUNDS

BRIEF DESCRIPTION OF THE INVENTION

The invention is a process for the preparation of 1,4-dihydroxy, 5,8-dihydronaphthalene and related compounds in accordance with the reaction

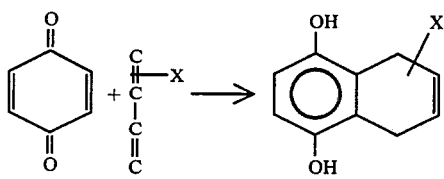

wherein X is selected from hydrogen, halogen, acyl and alkyl, in the presence of a ferric salt catalyst. The products are useful as antioxidants per se or as intermediates in the preparation of other antioxidants which may be used for the stabilization of various organic materials which are unstable in storage, during treatment and/or in use, and include motor fuel, jet fuel, diesel oil, mineral oil, lubricating oil, fuel oil, drying oil, greases, waxes, rubber, edible fats and oils, monomers including styrene butadiene, isoprene, actylenes, various unsaturated alcohols, acids and ketones.

DETAILED DESCRIPTION OF THE INVENTION

Referring now to the formulae, X may be a halogen such as chloro and bromo; 2 to 4 carbon acyl such as acetyl, propionyl and n-butyryl; and a 1–3 carbon alkyl such as methyl, ethyl and isopropyl. The substitution can be in the 1 or 2 position. Representative examples of substituted butadienes include:
1-acetyl-1,3-butadiene;
2-acetyl-1,3-butadiene;
1-chloro-1,3-butadiene;
2-chloro-1,3-butadiene;
1-methyl-1,3-butadiene;
2-methyl-1,3-butadiene;
1-ethyl-1,3-butadiene;
2-ethyl-1,3-butadiene;
1-bromo-1,3-butadiene; and
2-bromo-1,3-butadiene.

The catalyst used in the process is a ferric salt. The anion to form the salt may be selected from a number of inorganic and organic materials to include chloride, nitrate, carbonate, bicarbonate, sulfate, sulfide, phosphate, benzoate, naphthallate, toluate and phthalate. The amount of catalyst employed will depend upon the reactants but generally from about 3 molar % to about 9 molar % of the benzoquinone will be sufficient. A preferred range is from about 5 molar % to about 7 molar %.

Depending upon the reactants employed, it may be necessary to use a solvent. Typical solvents are the 1 to 4 carbon alcohols to include methanol, ethanol, propanol and butanol. Other suitable solvents are tetrahydrofurane and dioxane.

For best results, a slight excess of butadiene to benzoquinone is employed. Thus, while substantially equimolar amounts may be used, it is preferred that the molar ratio of benzoquinone to butadiene be from about 1:1.1 to 1:1.5.

The reaction can be conducted at a temperature between about 90° C. and about 120° C. at a pressure between about 4 atm. and about 10 atm. in a period of between about 6 hrs. and about 20 hrs. A preferred temperature range is between 90° C. and 110° C., and a preferred pressure range is between 4 atm. and 6 atm. Other conditions may be satisfactory, however, depending upon the particular catalyst and reactants employed.

The following examples will serve to illustrate the invention and preferred embodiments thereof. All parts and percentages in said examples and elsewhere in the specification and claims are by weight unless otherwise indicated.

EXAMPLE 1 p-Benzoquinone (3.0 g, 0.028 mole), 1,3-butadiene (1.0 g, 0.03 mole) and anhydrous $FeCl_3$ (0.20 g, 0.0013 mole) were dissolved into 40 ml absolute alcohol and placed in a thick reaction tube (O.D.⅝ 5/8 inches, wall 3/32 inches), and sealed. The tube was heated at 100° C. for 17 hours. The pressure was built up to 4–6 atm. during the reaction. Upon cooling the solution the solid precipitated and was isolated by filtration, and washed with diluted aqueous HCl and water. It was crystallized from acetone (m.p. 206° C.–208° C.) and identified as 1,4-dihydroxy, 5,8-dihydronaphthalene by I.R. measurement.

Yield 3.3 g, (76%).

EXAMPLE 2

The reaction was carried out under the same conditions as described in Example 1 except that the catalyst was iron phthalate formed in situ from $Fe(NO_3)_3$ (0.55 g, 0.0014 mole) and phthalic acid (0.23 g, 0.0014 mole). The product was filtered and identified as 1,4-dihydroxy, 5,8-dihydronaphthalene. Yield 3.5 g, (80%).

EXAMPLE 3

The reaction was carried out under the same reaction conditions as described in Example 1 except that the catalyst was $NiCl_2$ instead of $FeCl_3$. The solid isolated was found to be 1,4,5,8 tetrahydroanthraquinone, m.p. ,b 150° C.–155° C. Yield 2.2 g, (37%).

EXAMPLE 4

The reaction was carried out under the same conditions as described in Example 1 except that the catalyst was $CoCl_2$ instead of $FeCl_3$. The solid isolated was 1,4,5,8 tetrahydroanthraquinone, m.p. 150° C.–155° C. Yield 2.9 g, (50%).

EXAMPLE 5

The reaction was carried out using the same reaction conditions as described in Example 1 except that the catalyst was $Co(No_3)_2$ instead of $FeCl_3$. The solid isolated was 1,4,5,8 tetrahydroanthraquinone, m.p. 150° C.–155° C. Yield 2.7 g, (46%).

While the above disclosure is illustrative of the invention, numerous obvious variations may occur to one of ordinary skill and, accordingly, the invention is intended to be limited only by the appended claims.

What is claimed is:

1. A process for preparing compounds of the formula:

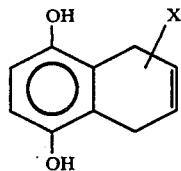

wherein X is selected from halogen, 2 to 4 carbon acyl, 1 to 3 carbon alkyl and hydrogen which comprises reacting benzoquinone with a 1,3-butadiene compound of the formula:

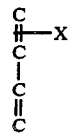

wherein X is as previously defined, in the presence of a catalytic amount of a ferric salt catalyst.

2. The process of claim 1 wherein the catalyst is iron phthalate.

3. The process of claim 1 wherein the catalyst is FeCl₃.

4. The process of claim 1 wherein the catalyst is Fe(NO₃)₃.

5. The process of claim 1 wherein a solvent is employed.

6. The process of claim 5 wherein the solvent is an alcohol.

7. The process of claim 1 wherein the reaction is conducted at a temperature between about 90° C. and about 120° C. and a pressure between about 4 atm. and about 10 atm.

* * * * *